United States Patent
Rosenberg (10) Patent No.: US 7,794,709 B2
(45) Date of Patent: Sep. 14, 2010

(54) APPARATUS AND METHODS FOR ENZYMATIC ESCHAROTOMY IN BURN INDUCED COMPARTMENT SYNDROME

(75) Inventor: Lior Rosenberg, Omer (IL)

(73) Assignee: MediWound Ltd., Yavne (IL)

( * ) Notice: Subject to any disclaimer, the term of this patent is extended or adjusted under 35 U.S.C. 154(b) by 502 days.

(21) Appl. No.: 10/970,023

(22) Filed: Oct. 21, 2004

(65) Prior Publication Data

US 2005/0202071 A1    Sep. 15, 2005

Related U.S. Application Data (63) Continuation of application No. PCT/IL03/00326, filed on Apr. 21, 2003.

(60) Provisional application No. 60/374,499, filed on Apr. 23, 2002.

(51) Int. Cl.
*A61K 38/48* (2006.01)

(52) U.S. Cl. .................. 424/94.65; 424/443; 424/447; 424/94.6; 424/94.63; 435/219; 435/212; 604/289; 604/290; 604/292; 604/304

(58) Field of Classification Search .................. None
See application file for complete search history.

(56) References Cited

U.S. PATENT DOCUMENTS

| | | | | |
|---|---|---|---|---|
| 4,197,291 A | | 4/1980 | Klein et al. ................... 424/94 |
| 4,226,232 A | * | 10/1980 | Spence ....................... 604/304 |
| 4,226,854 A | | 10/1980 | Klein et al. ................... 424/94 |
| 4,329,430 A | | 5/1982 | Klein et al. ................. 435/219 |
| 5,106,621 A | | 4/1992 | Rowan et al. ............. 424/94.65 |
| 5,196,196 A | | 3/1993 | Scott et al. ................ 424/94.64 |
| 5,260,066 A | | 11/1993 | Wood et al. ................. 424/447 |
| 5,342,287 A | * | 8/1994 | Jernoiu ........................... 602/3 |
| 5,387,517 A | | 2/1995 | Cini ............................. 435/212 |
| 5,830,739 A | | 11/1998 | Houck et al. ................ 435/219 |
| 5,897,517 A | * | 4/1999 | Laghi ........................... 602/62 |
| 6,335,427 B1 | | 1/2002 | Mynott et al. ............... 530/379 |
| 6,458,380 B1 | * | 10/2002 | Leaderman ................. 424/443 |

FOREIGN PATENT DOCUMENTS

| | | | |
|---|---|---|---|
| EP | 0194 647 | | 9/1986 |
| EP | 0296 787 | | 12/1988 |
| WO | WO 85/01439 | * | 4/1985 |
| WO | WO 98/53778 | * | 12/1998 |
| WO | WO 02/11624 | * | 2/2002 |

* cited by examiner

*Primary Examiner*—Allison M Ford
(74) *Attorney, Agent, or Firm*—Winston & Strawn LLP (57) ABSTRACT

Apparatus suitable for use in the prevention and treatment of burn induced compartment syndrome facilitates the rapid and efficient deployment of enzymatic compositions to the affected limb or limbs of a burn victim suffering from a circumferential burn. The apparatus includes a flexible, water-impermeable generally cylindrical covering layer. The covering layer has an inner surface facing the limb and an outer surface. The covering layer has a proximal sealable open end through which the burned limb is inserted and a distal closed end. An enzymatic escharotomy agent is contained within the covering layer. The covering layer retains the enzymatic escharotomy agent in close proximity to the burned limb, and the apparatus is enclosed within a sterile sealed package evacuated from moisture. In use, the burned limb is enclosed within the apparatus, and the enzymatic escharotomy agent is activated in situ by contacting the agent with hydrating fluid, thereby inducing enzymatic escharotomy of the circumferential burn.

18 Claims, 10 Drawing Sheets

FIG.1

FIGURE 2    Diagram of the CBID

APPARATUS AND METHODS FOR ENZYMATIC ESCHAROTOMY IN BURN INDUCED COMPARTMENT SYNDROME

CROSS REFERENCES TO RELATED APPLICATIONS

This application is a continuation of PCT Application No. PCT/IL03/00326, filed Apr. 21, 2003, which claims the benefit of U.S. Provisional Application No. 60/374,499, filed Apr. 23, 2002.

FIELD OF THE INVENTION

The present invention relates to an apparatus and methods suitable for use in the prevention and treatment of burn induced compartment syndrome, and to specifically designed application means for the rapid and efficient deployment of enzymatic compositions to the affected limb, or other part of the body of a burn victim, as well as to methods of using these compositions in conjunction with the application means.

BACKGROUND OF THE INVENTION

A major risk in deep circumferential burns and their characteristic rigid eschar is the development of Burn Induced Compartment Syndrome (BICS)[1,2]. Compartment syndrome (CS) is defined as a condition in which increased pressure in a confined anatomical space adversely affects the circulation and threatens the function and viability of the tissues therein (3). This condition requires urgent attention and resolution, sometimes as a component of the primary resuscitation of a burn victim.

The pressure develops in Compartment Syndrome as a result of extra vascular or extra cellular fluid collection within a confined space defined by non-compliant borders, which starts to develop immediately after the tissue burn injury occurred. As the intra-compartmental pressure increases, it progressively surpasses the closure pressures of lymphatic vessels, veins and venules, capillaries and arterial vessels, causing their collapse and obstructing flow[4]. Capillary closure pressure of 30 mmHg, is the accepted threshold pressure for defining a clinically meaningful compartment syndrome, which requires urgent therapeutic intervention[5,6]. The BICS stops the local blood supply to the tissue with the resulting ischemia and necrosis. The mounting pressure can cause additional pressure necrosis to pressure sensitive structures (such as nerves and muscles). The hands and feet crowded with neuromuscular structures close to the skin are the most vulnerable body areas but eventually even areas such as the neck, chest and abdomen will be compressed within the tight, armor-like hard eschar interfering with vital functions such as venous drainage and breathing.

The present Standard Of Care (SOC) treatment for deep circumferential burns is an emergency, early as possible surgical escharotomy that involves performing deep incisions through the non-resilient eschar from the edges of the intact skin down to healthy tissues thus relieving the mounting pressure. This surgical procedure is difficult, requires a skilled, specifically trained and experienced surgeon, and certain surgical facilities for effectuating the escharotomy that may involve acute complications such as bleeding. This surgical procedure may result in irreversible tissue damage and poor outcome. A delay in relieving the BICS (measured sometimes in a delay as short as a few hours) will result in a permanent damage to delicate structures such as nerves and muscles and extensive propagation of tissues necrosis. Better long-term results might have been achieved in many cases, if BICS could be resolved earlier and by a simple non skill-demanding procedure. Another theoretical optional treatment for deep circumferential burns is decompression of BICS by enzymatic debridement, which has been proposed in the past but no proof of feasibility of this concept has been reported[7,8].

Considerable attention has been focused in the use of proteolytic enzymes and other chemicals to effect early debridement of devitalized tissue, resulting from burns. Chemical agents, such as tannic acid, salicylic acid, and pyruvic acid, have not led to satisfactory debridement as theses chemical agents were found to cause further injury to already damaged tissue.

Extracts derived from the stem of the pineapple plant (Ananas Comosus) have been found to selectively and effectively remove devitalized tissue. Such extracts, also named bromelain, contain various proteolytic and hydrolytic enzymes. U.S. Pat. No. 4,197,291 discloses an enzyme product obtained from bromelain capable of debridement of devitalized tissue from a mammalian host which comprises a water soluble, protein that is free of caseinolytic activity and has a peak isoelectric point of about 6. A method for debridement of devitalized tissue using this enzyme product is disclosed in U.S. Pat. No. 4,226,854. U.S. Pat. No. 4,329,430 further discloses proteolytic enzyme mixtures derived from bromelain useful for dissecting and digesting devitalized tissue. The proteolytic mixture contains escharase, a water soluble, proteinaceous material, free of caseinolytic activity. Its peak isoelectric point is about 6 and is comprised of at least two subunits, each of which has a molecular weight from about 14.3 to 15 kDa. Additional components of the mixture have a molecular weight of from about 30 to 50 kDa. U.S. Pat. No. 5,830,739 describes isolation methods of escharase from bromelain, which yield an enzymatic preparation that is capable of debridement of devitalized tissue, but has neither proteolytic activity against denatured hemoglobin, gelatin, or casein nor hydrolytic activity against hyaluronic acid or dermatan sulfate.

U.S. Pat. No. 5,106,621 discloses purified cysteine proteinases derived from pineapple plant material having a molecular weight of about 25 kDa and exhibiting activity toward a coumarylamide substrate. Particularly, U.S. Pat. No. 5,106,621 relates to the cysteine proteinases ananain and comosain, which exhibit different physicochemical characteristics distinct from bromelain. A purified thiol activated protease, named o-Bromelain, is disclosed in U.S. Pat. No. 5,387,517, and is shown to have debridement activity. In addition, bromelain contains an acid phosphatase and a peroxidase and may contain amylase and cellulase activity. U.S. Pat. No. 6,335,427 teaches the purification of a 25 kDa protein from bromelain, the protein has been found to have anti-cancer activity.

EP 0296787 discloses absorbent adhesive dressings for use in treating wounds of the ulcer or burn type where there are significant wound exudates. Specifically, EP 296787 is concerned with a dressing made in the form of a three layer sandwich type construction having an occlusive film as the outer layer, an absorbent layer of fibers as the middle layer, and a wet-stick adhesive as the inner, wound-facing layer. The adhesive dressing may optionally contain a debriding enzyme on that part of the outer adhesive surface which contacts the wound.

EP 0194647 discloses a debriding tape, made from an occlusive or semi-occlusive, non-gel, non-bioerodible, surgical adhesive tape which contains on the adhesive mass surface of said surgical adhesive tape a debriding enzyme (either a proteolytic or a non-proteolytic enzyme useful for debridement of eschar and necrotic tissue) in dry, powdered form.

None of the above patents disclose an effective method or means for enzymatic escharotomy in burn induced compartment syndrome of a burned limb. There is an unmet need for application means and appropriate methods for rapid and efficient escharotomy using enzymatic escharotomy agents on the surface of burned skin area such as an affected limb or other body areas of a burn victim.

SUMMARY OF THE INVENTION

The present invention is related to an apparatus and methods for relieving Burn Induced Compartment Syndrome (BICS) by non-surgical, escharotomy using enzymatic escharotomy agents applied on the surface of a burned limb.

The non-surgical escharotomy achieved using the apparatus of the present invention provides various important advantages over the standard surgical escharotomy. The non-surgical escharotomy using the apparatus of the present invention can be performed by any unskilled personnel immediately after the damage occurs as the apparatus is ready for immediate use. Non-surgical escharotomy using the apparatus of the invention is able efficiently to prevent or relieve Burn Induced Compartment Syndrome before irreversible damage develops, and it is usually much more expeditious than bringing the victim to the appropriate facility and surgeon.

The present invention is based in part on the unexpected clinical and in vivo observations that Burn Induced Compartment Syndrome of burned skin tissue is relieved after treatment with certain enzymatic escharotomy agents applied by the apparatus of the present invention. In accordance with the present invention it is now disclosed that enzymatic escharotomy agents applied by the apparatus of the present invention provide safe, non-surgical, effective and rapid means for treating BICS in burned body areas. Importantly, in burn skin trauma, the development of irreversible damage such as BICS is prevented and the long-term prognosis for burn victims is improved.

The apparatus of the present invention offers novel means to perform an "automatic" or enzymatic escharotomy not depending on the availability of a skilled surgeon and surgical facilities. These means enable performance of non-surgical escharotomy of the more vulnerable and BICS-prone areas (hands and feet) immediately after the burn accident by any first-aid person. Immediate application of the apparatus of the present invention by any untrained person prevents the formation of the BICS. These crucial prerequisites dictate specific structural and functional features distinct from the past disclosed methods using proteolytic enzymes or other enzymes for debridement purposes, such as the method disclosed in U.S. Pat. No. 4,226,854 in which the enzymatic debridement agent is applied first following by covering that agent with a layer of material which is substantially impermeable to oxygen, which may be further coated with a flexible sheet of plastic.

The apparatus of the present invention comprising a flexible, water-impermeable covering layer, generally cylindrical or tube-shaped closed at one end and open at the other, and having an outer surface and an inner surface. An enzymatic escharotomy agent in an amount sufficient to induce enzymatic escharotomy is contained within the covering layer. The covering layer has a proximal sealable open end through which the burned limb is inserted and a distal closed end. The covering layer is capable of retaining said enzymatic escharotomy agent in close proximity to the burned limb. The enzymatic escharotomy is initiated after activating the enzymatic escharotomy agent by any hydrating means.

The enzymatic escharotomy agent contained within the covering layer of the present apparatus is in the non-activated lyophilized powder form. This allows the enzymatic escharotomy agent to be easily distributed relatively evenly on the inner surface of the covering layer. Thus, in a preferred embodiment, the covering layer already contains the enzymatic escharotomy agent in its lyophilized powder form prior to use, wherein the lyophilized powder is distributed at or adjacent to the inner surface of the covering layer in an amount effective to treat BICS. In another embodiment, an effective amount of the lyophilized powder is contained within an additional adsorbent layer adjacent to the inner surface of the covering layer. The apparatus of the present invention is enclosed within a sterile sealed package in order to avoid contact of the lyophilized powder with moisture.

In another embodiment, an effective amount of the lyophilized powder enclosed within the covering layer is combined with various excipients immediately prior to use. The enzymatic escharotomy agent is activated in situ by adding hydrating means that come into contact with the inner surface of the covering layer. Preferred hydrating means are for example physiological saline, purified water or any other suitable solution. In yet another embodiment, the hydrating means further comprise a chemical debriding agent to facilitate the enzymatic escharotomy. Such chemical debriding agents include for example acetic acid, pyruvic acid, phosphoric acid, salicylic acid, benzoic acid or malic acid.

Preferably, the hydrating means for activating the enzymatic escharotomy agents is used at 34-38° C. It is possible to use the invention even at room temperature, and the heat of the enclosed limb will generally suffice to elevate the temperature of the enzyme hydrating solution to around 34-38° C. Alternatively, according to another preferred embodiments the hydrating means may be preheated to approximately body temperature.

Alternatively and preferably, the enzymatic agents stored in the apparatus as a dried lyophilized powder further comprise additional excipients. Among these excipients, it is preferable to include viscosity-enhancing agents capable of forming a viscous solution from the lyophilized powder upon the addition of the hydrating means. The viscosity-enhancing agents may be for example synthetic polymers, natural polymers or any combinations thereof as are well known in the art.

The apparatus of the present invention may further comprise an external dressing layer adjacent or attached to the outer surface of the covering layer. The external dressing layer comprises at least one of a heat retaining cover, an elastic net or a pressure bandage.

According to a preferred embodiment of the invention, the enzymatic escharotomy agents are proteolytic enzymes. The proteolytic enzymes for use in conjunction with the apparatus of the invention may be derived from bacterial, vegetable or animal origin. In preferred embodiments the enzyme is selected from the group consisting of: enzymes derived from the pineapple including but not limited to bromelain or debridase; trypsin; fibrinolysin or fibrinolysin-deoxyribonuclease (such as the product known by the tradename Elase); *Clostridium histolyticum* enzyme H-4; collagenase (such as the product known by the tradenames Varidase or Sentyl); *Bacillus subtilis* enzyme sutilains; *Streptococci* enzymes streptokinase or streptodornase; derivatives of papaya including papain or papain-urea (such as that known by the tradename Accuzyme); and enzymes derived from krill$_{(9)}$.

The present invention further relates to methods for using the apparatus disclosed herein for applying enzymatic escharotomy agents in order to prevent BICS following burn trauma. Specifically, one embodiment the present invention relates to a method for inducing enzymatic escharotomy of a circumferential burn in an affected limb comprising the steps of:

(a) enclosing the limb with the apparatus of the invention, and
(b) activating said enzymatic escharotomy agent in situ by contacting said enzymatic escharotomy agent with hydrating means; thereby inducing enzymatic escharotomy of said circumferential burn.

In another embodiment, the present invention relates to a method for treating Burn Induced Compartment Syndrome in a burned limb comprising the steps of:

(a) enclosing the limb with the apparatus of the invention, and
(b) activating said enzymatic escharotomy agent in situ by contacting said enzymatic escharotomy agent with hydrating means; thereby relieving the Burn Induced Compartment Syndrome in said burned limb.

In accordance with one aspect of the present invention, the apparatus of the invention comprises a suitable covering layer for enveloping or enclosing a body area with a burn, such as a limb of a burn victim. The apparatus of the invention is especially useful in treating a subject suffering from circumferential burns. The apparatus of the invention comprises a suitable covering layer, said covering layer comprising at least one effective enzymatic escharotomy agent in an effective amount to prevent BICS. According to various embodiments of the invention, said covering layer is sterile and water-impermeable thereby rendering it capable of retaining an aqueous solution or suspension. Additionally and preferably the covering layer is elastic or pliant so as to accommodate itself to the contours of the limb. More preferably it is sufficiently flexible to accommodate itself to the contours of the limb without causing friction or abrasion.

In accordance with a currently most preferred embodiment, the suitable covering layer is in the form of a flexible, sterile, water impermeable sleeve-like dressing that contains the non-activated enzymatic escharotomy agents. The sleeve-like dressing is capable of retaining the enzymatic escharotomy agents in close proximity to the body area that it encloses. The sleeve-like dressing may further comprises a retaining cover, an elastic net or any other layers, in addition to the essential water impermeable layer.

These and further embodiments will be apparent from the detailed description and examples that follow.

DETAILED DESCRIPTION OF THE INVENTION

The apparatus disclosed herein is useful in the prevention and treatment of burn induced compartment syndrome (BICS) using enzymatic, non-surgical escharotomy. The apparatus of the present invention comprises application means for the rapid and efficient deployment of the enzymatic escharotomy agents to the affected limb or limbs of a burn victim. In accordance with the principles of the present invention it is now disclosed that enzymatic escharotomy provides safe effective and rapid means for prevention and treatment of BICS.

Compartment syndrome (CS) is defined as a condition in which increased pressure in a confined anatomical space adversely affects the circulation and threatens the function and viability of the tissues therein$_{(3)}$. The pressure develops as a result of extra vascular or extra cellular fluid collection within a confined space defined by non-compliant borders. As the intra-compartmental pressure increases, it progressively surpasses the closure pressures of lymphatic vessels, veins and venules, capillaries and arterial vessels, causing their collapse and obstructing flow and resulting in ischemia and pressure necrosis$_{(4)}$. Capillary closure pressure of 30 mmHg is the accepted threshold pressure for defining a clinically meaningful compartment syndrome, which requires therapeutic intervention$_{(5,6)}$.

Burn Induced Compartment Syndrome can form as a result of progressive tissue edema of a severely burned limb, which is enveloped in non-compliant rigid burn eschar$_{(2,5)}$. The classic symptoms and signs of CS (pain, pallor, paresthesia and hypothermia) may be masked by the clinical expression of the burn wound itself, making the early diagnosis of BICS difficult. Lack of distal arterial pulses cannot be used as a sign for early diagnosis. When present, a significant neuromuscular damage is usually found$_{(10)}$.

Compartment syndrome is resolved when the compartmental pressure is lowered below 30mmHg. The accepted therapy for BICS is the early performance of surgical escharotomy, creating full thickness longitudinal transections throughout the whole eschar length. The surgical cleavage of the rigid eschar increases the compliance of the compartment's envelope, allowing volume increase of the edematous tissue that result in pressure relief Obviously, such a surgical procedure can be performed only by highly trained and skilled surgeon with adequate facilities to perform the procedure and take care of its potential complications such as uncontrolled bleeding and contamination.

The apparatus of the present invention comprising a flexible, water-impermeable generally cylindrical or tube shaped covering layer, said covering layer having an inner surface facing the limb and an outer surface. An enzymatic escharotomy agent is contained within said covering layer while the covering layer is capable of retaining said enzymatic escharotomy agent in close proximity to the burned limb.

The inventor discloses herein that the apparatus of the invention which preferably comprises Debridase as enzymatic escharotomy agent, conforms to the basic criteria of an adequate escharotomy means for the prevention and treatment of compartment syndrome in burn victims. The resolution of this emergency medical condition can be achieved without surgical intervention and without the danger of exposing the already badly injured patient to any additional trauma. This treatment does not require any special surgical skills or facilities and therefore can be provided very early after the initial trauma by paramedical personnel or other aid providing personnel. It is effective in reducing compartmental pressure in affected limbs in less than an hour.

The enzymatic escharotomy agent for use in conjunction with the apparatus of the invention may be an enzyme of bacterial, vegetable or animal origin. In preferred embodiments the enzyme is selected from the group consisting of: enzymes derived from the pineapple including but not limited to bromelain or debridase; trypsin; fibrinolysin or fibrinolysin-deoxyribonuclease (also known by the tradename Elase); *Clostridium histolyticum* enzyme H-4; Collagenase also known by the tradenames Varidase or Sentyl; *Bacillus subtilis* enzyme Sutilains; *Streptococci* enzymes streptokinase or streptodomase; derivatives of papaya including papain or papain-urea also known by the tradename Accuzyme; and enzymes derived from krill$_{(9)}$.

Debridase is an enzyme mixture extracted from Bromelain, capable of effective, rapid (3-4 hours) and selective burn eschar debridement, sparing surrounding vital tissue. Bromelain is a known enzyme mixture, extracted from pineapple stems, that has been reported to be useful for eschar debridement$_{(10)}$. One selective ingredient was isolated from bromelain in 1983 and named "Escharase"$_{(11)}$. Escharase is a non proteolytic enzyme made of three 15,000 Dalton subunits which is thought to cause activation of Tissue Collagenase which in turn attacks the denatured Collagen of the damaged tissue, creating a plane of cleavage between vital tissue and damaged tissue, enabling eschar separation$_{(12)}$. The isolated Escharase is not effective on burns in vivo since it lacks the proteolytic activity necessary to reach the interface of the vital and damaged tissues. Escharase can exert its effect in combination with proteolytic enzymes, such as are present in Debridase, of which 1-2% is Escharase.

The enzymatic escharotomy agents useful in the present invention include all of the known materials which have been used previously for enzymatic debridement of non-vitalized tissue. U.S. Pat. No. 3,983,209 discloses that proteolytic enzymes useful for debridement of eschar and necrotic tissue to permit wound healing include papain, trypsin, collagenase, subtilisins A and B, ficin, pepsin, lysozyme, streptokinase, fibrinolysin, Pinguinain, and bromelain or their active fractions. Other known debriding enzymes include papain, the "escharase" fraction of bromelain, pepsin, chymotrypsin, pancreatic lipase, n-acetylcysteine. Particular enzyme products derived from bromelain are taught in U.S. Pat. Nos. 4,197,291, 4,307,081 and 4,361,551.

The apparatus of the present invention provides a non-surgical escharotomy means which is simple to use by any help provider and can be applied on the burned area as part of the basic initial first aid. The use of the present apparatus for non-surgical escharotomy prevents or minimizes possible complications of surgical escharotomy such as hemorrhage, increase of fluid loss, subcutaneous infection, severance of neuromuscular bundles, severance of tendons and muscular damage (11,12). The use of the present apparatus for non-surgical escharotomy prevents the escalating cascade of the BICS, whereas even a short delay may result in irreversible damage to the affected limb, and resultant loss of function.

The enzymatic escharotomy agents contained in the apparatus of the present invention are solids capable of being ground into powder form. This allows them to be easily distributed relatively evenly within the covering layer.

In this embodiment the apparatus can be stored for prolonged periods of time in moisture-free conditions and brought easily to the scene of accident to be available for use. The escharotomy agent is activated in situ by the addition of an aqueous solution, such as physiological saline, purified water and any other suitable solution. Preferably the enzymatic agent may be stored for use in the apparatus as a dried powder further comprising a viscosity-enhancing agent that will form a gel or emulsion or other viscous solution upon hydration with hydrating means. The viscosity-enhancing agent may include synthetic polymers, natural polymers or any combinations thereof as are well known in the art.

The quantities of the enzymatic escharotomy agent contained within the apparatus of the invention do not depend on the depths and severity of the burn to be treated. It is desired to use an effective amount of the particular enzymatic escharotomy agent. Generally it is desirable to use more than the minimum amounts specified so that the escharotomy is completed within as short a period of time as possible. However, if the amount of debriding enzyme applied is too great, then it is possible that the escharotomy will cause blood loss because the vessel walls may be lysed by the enzyme.

According to the principles of the invention said covering layer is generally sterile and water-impermeable thereby rendering it capable of retaining an aqueous solution or suspension. Additionally and preferably the covering layer is elastic or pliant so as to accommodate itself to the contours of the limb. More preferably it will be sufficiently flexible to accommodate itself to the contours of the limb without causing friction or abrasion.

The covering layer which is useful for purposes of the present invention may be any water-impermeable polymeric film commonly used for medical, surgical or tape purposes. Examples of polymeric films are polyethylene films such as polypropylene, polyurethane, polyester or vinyl. An evaporative covering layer cannot be used since it allows moisture to evaporate through the covering layer, which results in drying and inactivation of the enzymatic escharotomy agent so that it is no longer effective.

The enzymatic escharotomy agents of the present invention are not effective in their dry state, but only are activated when they are exposed to the hydrating means such as water. The enzymatic escharotomy agents may be activated by applying water to the burned limb just before applying the covering layer on top of the limb. In another embodiment, the water is applied into the covering layer in order to activate the enzymatic escharotomy agents contained therein.

It is desirable that the impermeable covering layer used in the present apparatus is transparent. The advantage of a transparent covering layer is to permit inspection of the burned limb during the enzymatic escharotomy process without painful removal of the covering layer.

The enzymatic escharotomy agents contained within the covering layer, may adhere to the inner surface of the covering layer. The lyophilized powder comprising the enzymatic agents may adhere to the inner surface of the covering layer through electrostatic forces or using an appropriate adhesive. The specific nature of the adhesive is not critical as long as it is acceptable for medical or surgical purposes, it does not react with or inactivate the enzymatic escharotomy agents, and is capable of holding the enzymatic escharotomy agents powder particles in place. Naturally adhesives which do not adversely affect the skin are preferred. Of course, patients with burns are in a sensitive condition so it is desired that any adhesive which will contact the very tender areas be easy to remove and not cause any undue pain or skin damage.

The apparatus of the present invention can be sterilized in a manner which will not inactivate or activate the enzymatic escharotomy agents prematurely, for example by irradiation, or any other means as is well known in the art. The apparatus of the present invention can be sterilized in sealed packages and be available for actual use, whenever desired, in its sterile form.

The enzymatic escharotomy agents of the present invention in their lyophilized form are stable at room temperature and need not be refrigerated, when packaged in a sealed waterproof container in order to maintain their sterility and moisture-free conditions. This is a great advantage for use under emergency conditions, and even in hospitals.

Figure 1:
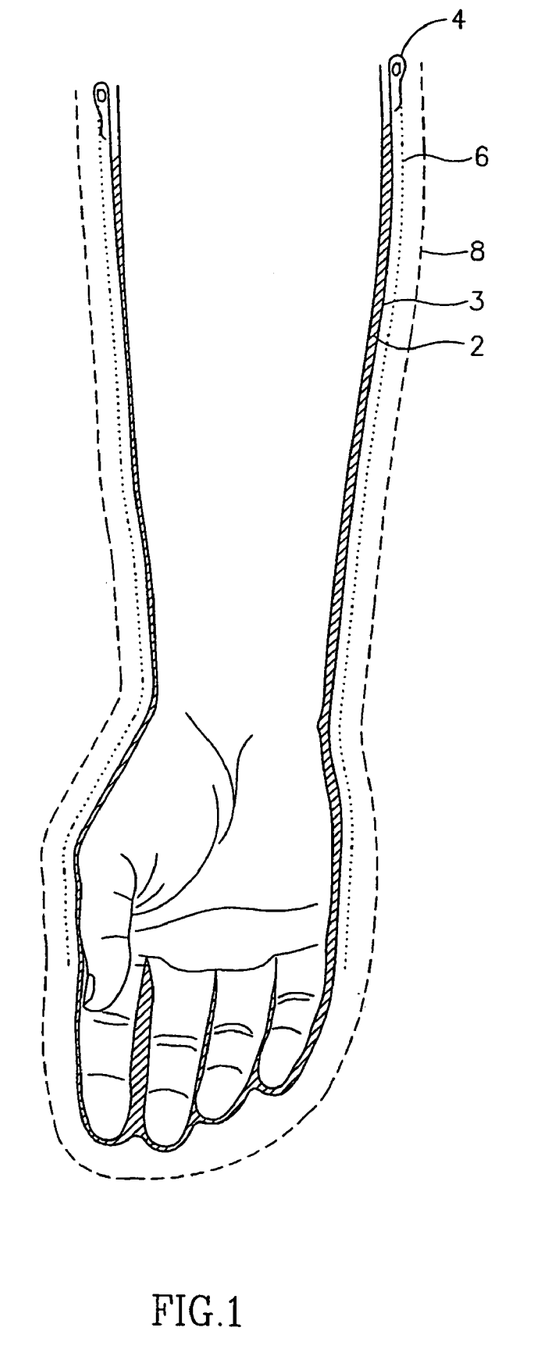
FIG. 1 depicts schematically an example of the device for enzymatic escharotomy of a limb area suitable for rapid application of the enzymatic treatment to the limb of a burn victim even before hospitalization.

In accordance with a currently most preferred embodiment, depicted schematically in FIG. 1 for use for the hand and for the arm, the application means will be in the form of a flexible, sterile, water impermeable "sleeve-like" dressing (3) that contains the non-activated enzymatic escharotomy agent (2). The application means is capable of retaining the enzymatic debridement agent in close proximity to the limb that it encloses. The dressing or "sleeve" of the application means may further comprise a heat retaining cover (8), an elastic net (6) or any other layers, in addition to the essential water impermeable layer (3). The open end of the application means, into which the limb is inserted will advantageously be sealable or at least partially sealable, by sealing means (4) which can be retained sufficiently close to the surface of the limb to prevent the leakage of the enzymatic debridement means. In its simplest embodiments the sealing means can be a drawstring or an elastic band near to the open end of the sleeve-like application means with or without adhesive padding that adheres to the skin. Further optional features include a second netlike covering or a heat retaining covering that may also be adapted to maintain the water impermeable layer in close proximity to the limb that is to be encased in the application means.

It will be recognized by the skilled artisan that the volume of the limb may differ significantly from patient to patient, or between upper limbs and lower limbs. Nevertheless, the combination of the flexible internal water impermeable layer, together with one or more retaining means will be sufficiently adaptable to afford a reasonable volume to serve any individual case.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Inducing a Circumferential Burn using Circumferential Burn Infliction Device (CBID)

Figure 2:
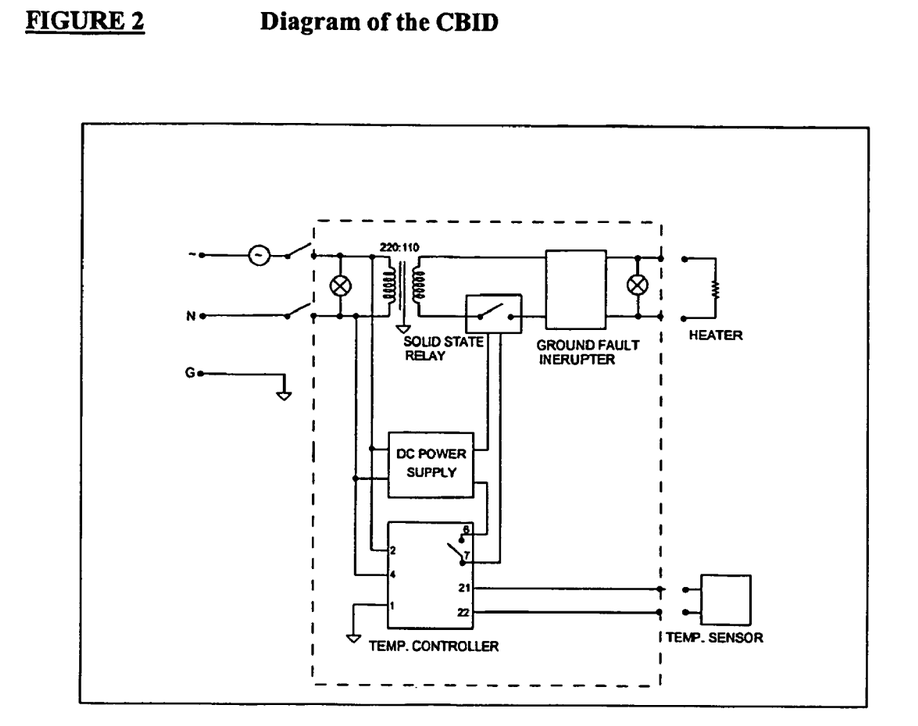
FIG. 2 is the schematic representation of the circumferential burn infliction device (CBID).

The Circumferential Burn Infliction Device (CBID) exemplified herein below has shown an excellent ability to stabilize accurately a preset temperature after "studying" the thermal properties of the heated object. The flexible heating unit enables it to conform intimately to irregular surfaces. The combination of the flexible heating element and the accurate controlling system allows the infliction of controlled, uniform, predictable and reproducible burns on irregular surfaces of circular bodies. The CBID shown diagrammatically in FIG. 2. It is based on a temperature controlled flexible heater wrapped around the limb.

Example 2

An Animal Model for Burn Induced Compartment Syndrome

In order to establish the general utility of enzymatic escharotomy for the prevention and treatment of compartment syndrome in burn victims, the inventor devised an experimental and measurable animal model for burn induced compartment syndrome, and performed animal studies on circumferential thermal burns. Having established the model's validity, the inventor and his collaborators have used it for a preliminary study of the efficacy of enzymatic escharotomy as an optional treatment for burn induced compartment syndrome of the limbs. The pressure measurement system disclosed herein may also be used for continuous monitoring of compartmental pressure in high risk patients and provide means for early detection.

Of all animals examined, the pigskin has the greatest resemblance to a human skin: morphologically, functionally and in thermal characteristic$_{(13)}$. For these reasons pigskin is accepted as an experimental model for the study of burns$_{(14-16)}$. A full thickness circumferential burn at the proximal part of a pig's leg, leads to the formation of a compartment syndrome distally which its severity can be evaluated by direct pressure measurements of the anterior compartment of the leg.

The study subject was a 20 kg white domestic pig. Anesthesia was induced by intramuscular Ketamine 15 mg/kg and intramuscular Diazepam 2 mg/kg, and the animal was put in a specially designed hammock to allow convenient accessibility to the animal's head and legs. After introduction of an endo-tracheal tube anesthesia was maintained with Halothane. Pulse, respiratory rate and pulse oximetry were used for monitoring$_{(17)}$. Anterior compartment pressure was measured continuously using a pediatric I.V. butterfly needle located in the anterior compartment and connected to a pressure transducer. The pressure values were displayed digitally and graphically on a Mennen "Horizon 1000" monitor.

After clipping the hair from the legs with an electric hair clipper, full thickness circumferential burns were inflicted to the proximal part of the legs. The burns were inflicted by the CBID set for temperature of 110° C. and exposure time of 150 seconds. 60 minutes after burn infliction the burn wounds of the left legs were mechanically scrubbed to remove the charred keratin and bandaged with an occlusive dressing containing aqueous gel and 2 gr. Debridase. The burn wounds of the right legs were mechanically scrubbed to remove the charred keratin and bandaged with an occlusive soaking dressing (NaCl 0.9%). A surgical escharotomy was performed on the burn wounds of the right legs 120 minutes after burn infliction. Sterile dressing was applied to all burn wounds at the end of the trial and Suppository of Voltaren 50 mg was given as an analgesic.

The procedure described above was repeated four more times. Surgical escharotomy was performed on the burn wounds of the right legs 240 minutes after burn infliction as the quick recovery of normal pressure seen after performing surgical escharotomy have allowed a safe prolongation of the ischemia time.

Experimental Results

Circumferential Burn Inflication Device (CBID)

Figure 3:
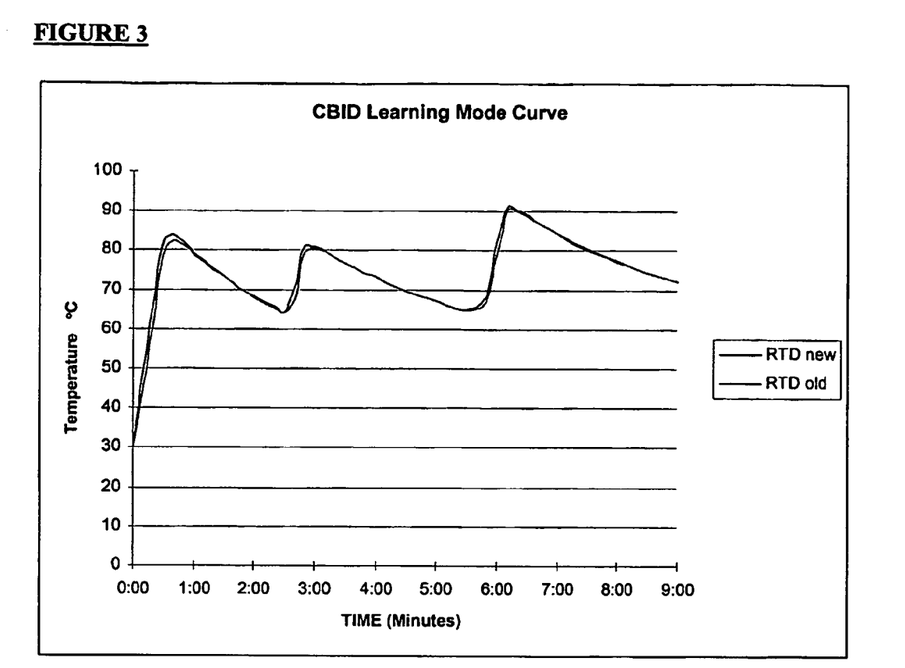
FIG. 3 demonstrates three cycles of heating and cooling comprising the learning process.

FIG. 3 demonstrates three cycles of heating and cooling comprising the learning process. The CBID studies the thermal characteristics of the heated object and automatically sets the appropriate system parameters: P—Proportional Band, I—Integral Band, D—derivative time, N—anti reset windup. The heating parameters can also be programmed manually FIG. 4 demonstrates the temperatures measured by the two temperature probes during heating and temperature stabilization in the same experimental setup studied by the CBID. The goal temperature was set at 70° C.

Figure 4:
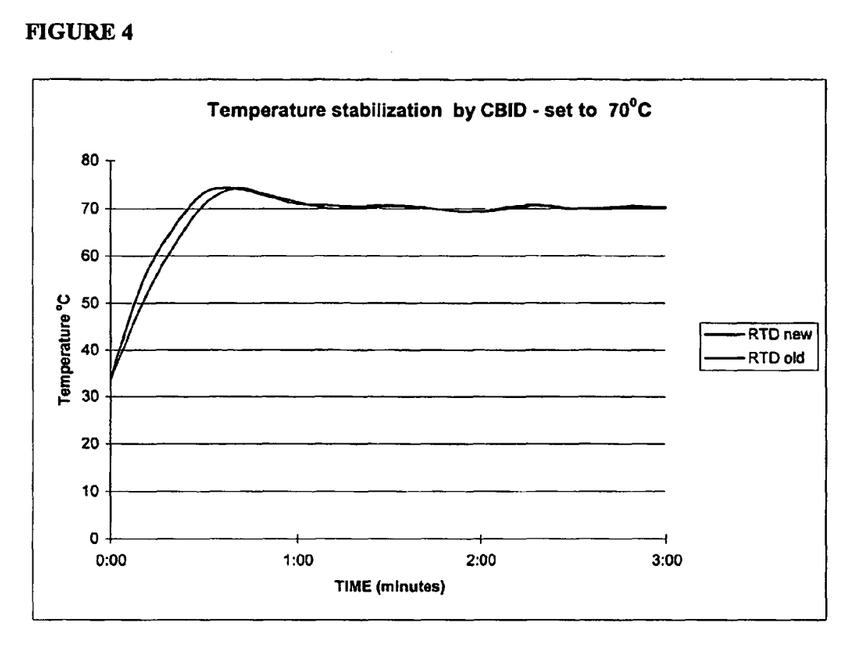
FIG. 4 demonstrates the temperatures measured by the two temperature probes during heating and temperature stabilization in the experimental setup studied.

A good temperature stabilization [70° C.±6° C.] was demonstrated at the end of a rapid heating process with a short period of overheating to 74° C.

After inflication of deep circumferential burn to the animal's limbs the intracompartment pressure in the anterior compartment rose above 30 mmHg—to meet the criteria defining Compartment Syndrome$_{(5,6)}$. Areas distal to the burn have demonstrated the typical changes: cyanotic color, temperature decrease, edema and swelling. The Anterior Compartment intra-compartmental pressures that were measured at the different stages of the experiment were in correlation with the typical clinical condition. The entire picture of pre-burn baseline pressure, the pressure increase following burn inflication, its stabilization over 30 mmHg, and the immediate pressure decrease following escharotomy were all in concordance with this clinical entity implying a successful reconstruction of an experimental animal model for burn induced compartment syndrome.

The Evaluation of the Efficacy of Enzymatic Escharotomy in Resolving Burn Induced Compartment Syndrome.

Safety

Previous animal and clinical studies have shown that the Debridase composition is locally and systemically safe. In an aqueous solution (the activated form of the enzyme) the activity of the enzymes diminishes quickly, after 4 hours the mixture is practically inactive. An unintentional or accidental prolonged application will cause no harm. The safety range of the effective dose is very wide from half the optimal dose (2 gr. for 100 per cm of eschar) of dry enzyme up to more than its double. No effect was seen on healthy unharmed tissue. The application of Debridase does not require any special skills or facilities and the enzymatic escharotomy with Debridase is simple and can be performed by any member of the medical and paramedical personnel.

Efficacy

Clinical signs and pressure measurement, the hallmarks of compartment syndrome distal to the inflicted deep circumferential burn were demonstrated. The pressure average in the limbs of the untreated group has remained above the threshold pressure of 30 mmHg, necessary for the definition of a compartment syndrome, for the entire duration of the experiment. Surgical escharotomy at termination has caused a rapid return to normal pressure—identical to the baseline pressure, followed by a significant improvement in clinical signs.

The pressure average of the treated limbs have dropped below the threshold pressure of 30 mmHg, 30 minutes after Debridase application and has remained below this value for the entire duration of the experiment. At the end of the 4-hour experiment the pressure average was close to the baseline pressure. Upon bandage removal, no clinical signs of schema were evident. The necrotic tissue was consumed by the Debridase debriding agent leaving a viable tissue at the wound's bed.

Speed

Both methods of surgical and enzymatic escharotomy have achieved complete resolution of the compartment syndrome and restored normal pressure in the affected limb. Surgical escharotomy have resulted in an immediate pressure drop. The pressure average in the limbs of the Debridase treated group has dropped below 30 mmHg after 30 minutes of enzymatic treatment and has remained normal (baseline pressure) for the entire duration of the experiment. If performed simultaneously, the surgical escharotomy will relive the BICS faster when performed by an experienced burn surgeon in an appropriate facility. However, in the real clinical setup it is difficult to assess the average time needed to achieve an effective escharotomy. Theoretically it may be only a few minutes, if an experienced burn surgeon can be found close to the scene of the accident, but it might take much longer. Since application of Debridase to deep circumferential burns is safe and easy, it may be performed early as part of the primary pre-hospital treatment by properly trained personnel. As it can be used immediately even before evacuation with significant results after 30 minutes, enzymatic escharotomy may provide an overall faster treatment compared to the surgical escharotomy.

Changes in the measured intracompartmental pressure have preceded the changes in clinical appearance both in the post burn-inflication phase and in the decompression phase. A continuous monitoring of compartmental pressure with a similar measuring system in clinical setup, may serve as a sensitive mean for the early detection of a developing BICS.

An Animal Model for burn Induced Compartment Syndrome.

Table 1 contains the pressures measured in the anterior limb compartments. Time is measured in minutes after burn inflication.

The pressure measurements at t=0 are the pressures measured in the anterior compartment of the respective limb before burn inflication and represent the baseline pressure. Enzymatic escharotomy has began at t=60 on the left sided limbs. Surgical escharotomy was performed at t=120 on the right sided limbs.

Figure 5:
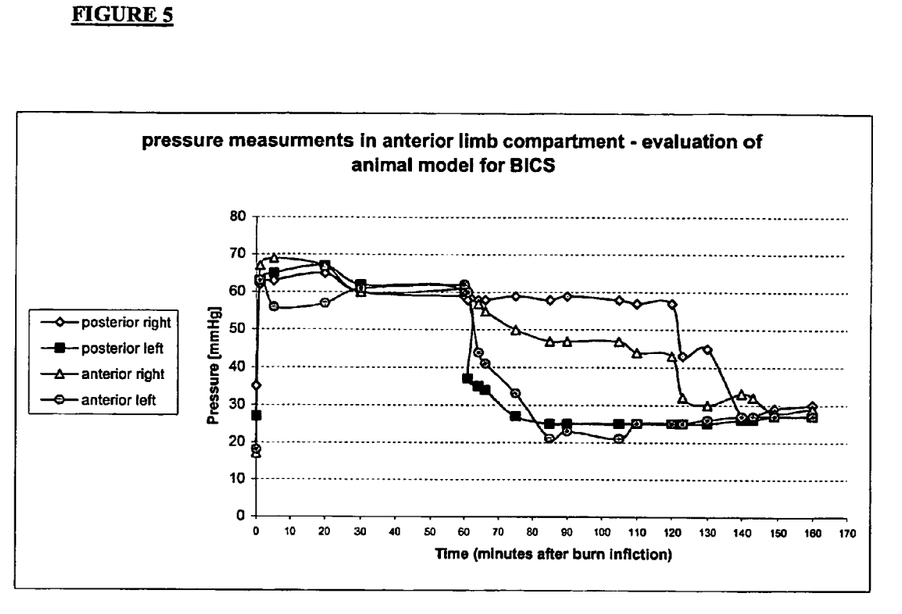
FIG. 5 contains a graphic representation of the measurements in the experimental setup.

FIG. 5 contains a graphic representation of the measurements.

TABLE 1

Pressures measurements in mmHg in pig limbs

| Time | posterior right | posterior left | anterior right | anterior left |
|---|---|---|---|---|
| 0 | 35 | 27 | 17 | 18 |
| 1 | 62 | 63 | 67 | 63 |
| 5 | 63 | 65 | 69 | 56 |
| 20 | 65 | 67 | 67 | 57 |
| 30 | 60 | 62 | 60 | 61 |
| 60 | 59 | 60 | 61 | 62 |
| 61 | 58 | 37 | 61 | 60 |
| 64 | 58 | 35 | 57 | 44 |
| 66 | 58 | 34 | 55 | 41 |
| 75 | 59 | 27 | 50 | 33 |
| 85 | 58 | 25 | 47 | 21 |
| 90 | 59 | 25 | 47 | 23 |
| 105 | 58 | 25 | 47 | 21 |
| 110 | 57 | 25 | 44 | 25 |
| 120 | 57 | 25 | 43 | 25 |
| 123 | 43 | 25 | 32 | 25 |
| 130 | 45 | 25 | 30 | 26 |
| 140 | 27 | 26 | 33 | 27 |
| 143 | 27 | 26 | 32 | 27 |
| 149 | 29 | 27 | 28 | 27 |
| 160 | 30 | 27 | 29 | 27 |

The Evaluation of the Efficacy of Enzymatic Escharectomy in Resolving Burn Induced Compartment Syndrome.

Table 2 contains the values of anterior compartmental pressure that where measured.

TABLE 2

| | Exp. No. | | | | | | | | | |
|---|---|---|---|---|---|---|---|---|---|---|
| | 1 | 2 | 3 | 4 | 5 | 1 | 2 | 3 | 4 | 5 |
| | Measured anterior compartment pressure [mmHg] in untreated limbs - Rt. | | | | | | | | | |
| Time | Posterior limbs | | | | | Anterior limbs | | | | |
| 0 | 35 | 23 | 20 | 16 | 8 | 17 | 14 | 23 | 8 | 18 |
| 60 | 59 | 58 | 66 | 30 | 42 | 61 | 56 | 82 | 30 | 30 |
| 75 | 59 | 50 | 61 | 31 | 28 | 50 | 57 | 71 | 32 | 23 |
| 90 | 58 | 49 | 50 | 28 | 25 | 49 | 57 | 50 | 29 | 25 |
| 110 | 57 | 52 | 39 | 29 | 31 | 44 | 56 | 56 | 31 | 26 |
| 120 | 57 | 50 | 40 | 28 | 31 | 43 | 57 | 53 | 30 | 27 |
| 130 | 45 | 48 | 40 | 28 | 33 | 30 | 58 | 54 | 32 | 27 |
| 150 | 29 | 47 | 36 | 28 | 57 | 28 | 53 | 50 | 31 | 27 |
| 160 | 30 | 46 | 33 | 32 | 56 | 29 | 52 | 43 | 37 | 27 |
| 170 | | 46 | 39 | 31 | 55 | | 53 | 58 | 34 | 27 |
| 180 | | 46 | 30 | 30 | 57 | | 52 | 41 | 33 | 27 |
| 210 | | 41 | 29 | 30 | 68 | | 26 | 40 | 33 | 26 |
| 220 | | 33 | 28 | 31 | 69 | | 25 | 42 | 38 | 26 |
| 230 | | 31 | 28 | 29 | 69 | | 25 | 41 | 35 | 26 |
| | Measured anterior compartment pressure [mmHg] in untreated limbs - Lt. | | | | | | | | | |
| Time | Posterior limbs | | | | | Anterior limbs | | | | |
| 0 | 27 | 21 | 20 | 14 | 19 | 18 | 16 | 23 | 7 | 11 |
| 60 | 60 | 32 | 72 | 26 | 50 | 62 | 43 | 69 | 26 | 28 |
| 75 | 27 | 32 | 58 | 28 | 34 | 33 | 37 | 29 | 29 | 22 |
| 90 | 25 | 30 | 46 | 23 | 33 | 23 | 39 | 17 | 25 | 19 |
| 110 | 25 | 34 | 36 | 24 | 31 | 25 | 37 | 14 | 27 | 18 |
| 120 | 25 | 34 | 37 | 22 | 30 | 25 | 37 | 14 | 25 | 17 |
| 135 | 25 | 32 | 36 | 22 | 30 | 26 | 34 | 13 | 26 | 17 |
| 150 | 27 | 33 | 35 | 22 | 29 | 27 | 34 | 12 | 26 | 16 |
| 160 | 27 | 32 | 31 | 28 | 28 | 27 | 34 | 12 | 31 | 16 |
| 170 | | 32 | 39 | 25 | 28 | | 36 | 15 | 29 | 15 |
| 180 | | 30 | 31 | 24 | 27 | | 34 | 10 | 28 | 15 |
| 210 | | 26 | 30 | 25 | 27 | | 20 | 12 | 29 | 15 |
| 220 | | 26 | 32 | 30 | 26 | | 20 | 13 | 34 | 15 |
| 230 | | 26 | 31 | 27 | 26 | | 20 | 13 | 32 | 14 |

Figure 6:
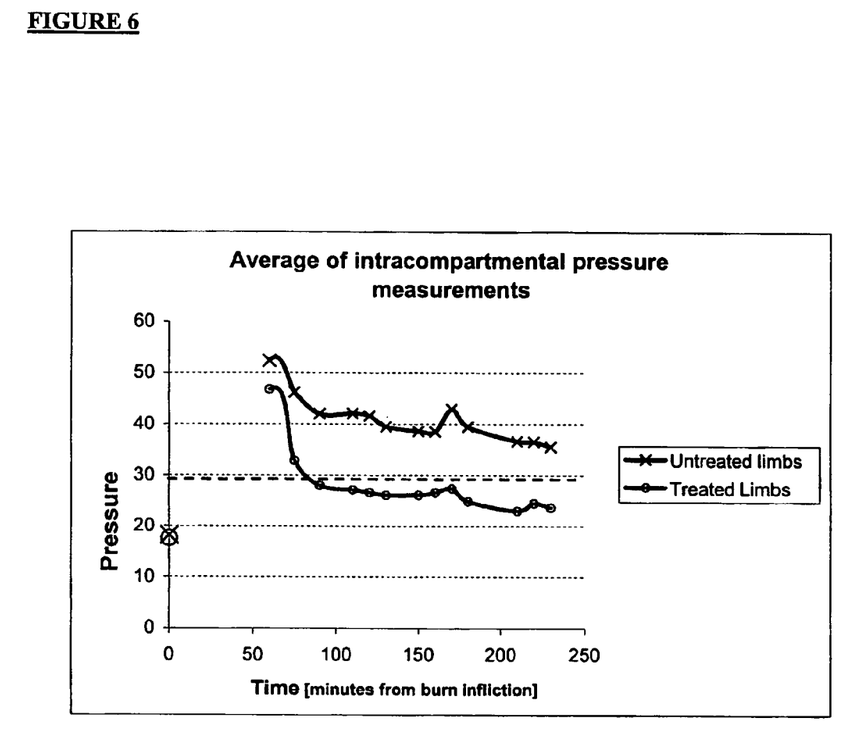
FIG. 6 is a graphic representation of the pressure averages as displayed. The pre-burn pressure averages are identical in both groups.

Table 3 contains the calculated averages of the measured pressures and the respective standard deviation. The graphic representation of the pressure averages is displayed in FIG. 6. The pre-burn pressure averages are identical in both groups. The different profile of the pressures averages is noticeable and statistically significant (p=0.0001).

TABLE 3

| | Untreated limbs - Rt. | | Treated limbs - Lt. | |
|---|---|---|---|---|
| Time | Avareage | Standard deviation | Avareage | Standard deviation |
| 0.0 | 18.2 | 7.9 | 17.6 | 5.9 |
| 60.0 | 52.4 | 18.6 | 46.8 | 18.2 |
| 75.0 | 46.2 | 16.5 | 32.9 | 9.8 |
| 90.0 | 42.0 | 13.5 | 28.0 | 9.1 |
| 110.0 | 42.1 | 12.5 | 27.1 | 7.5 |
| 120.0 | 41.6 | 12.1 | 26.6 | 7.9 |
| 130.0 | 39.5 | 11.2 | 26.1 | 7.3 |
| 150.0 | 38.6 | 11.8 | 26.1 | 7.6 |
| 160.0 | 38.5 | 10.2 | 26.6 | 7.1 |
| 170.0 | 42.9 | 11.8 | 27.4 | 8.8 |
| 180.0 | 39.5 | 11.3 | 24.9 | 8.3 |
| 210.0 | 36.6 | 13.9 | 23.0 | 6.6 |
| 220.0 | 36.5 | 14.4 | 24.5 | 7.8 |
| 230 | 35.5 | 14.5 | 23.6 | 7.2 |

Figure 7:
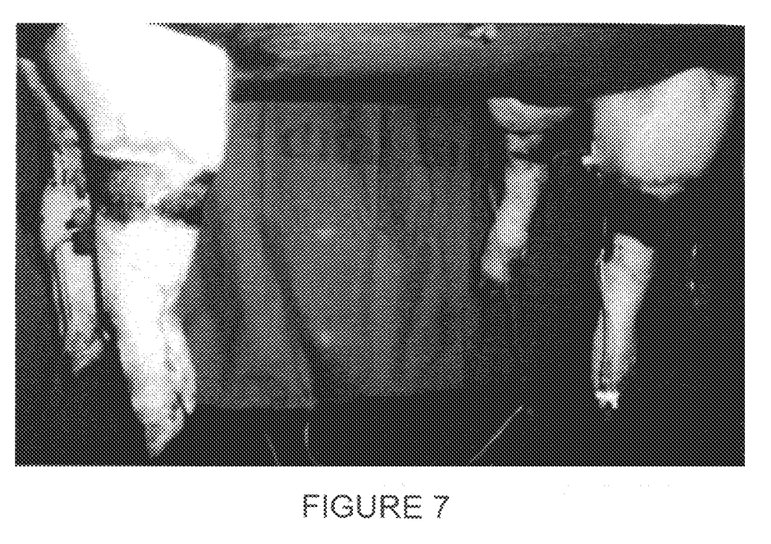
FIG. 7 demonstrates the burned limbs of the anesthetized experimental animal.
Figure 8:
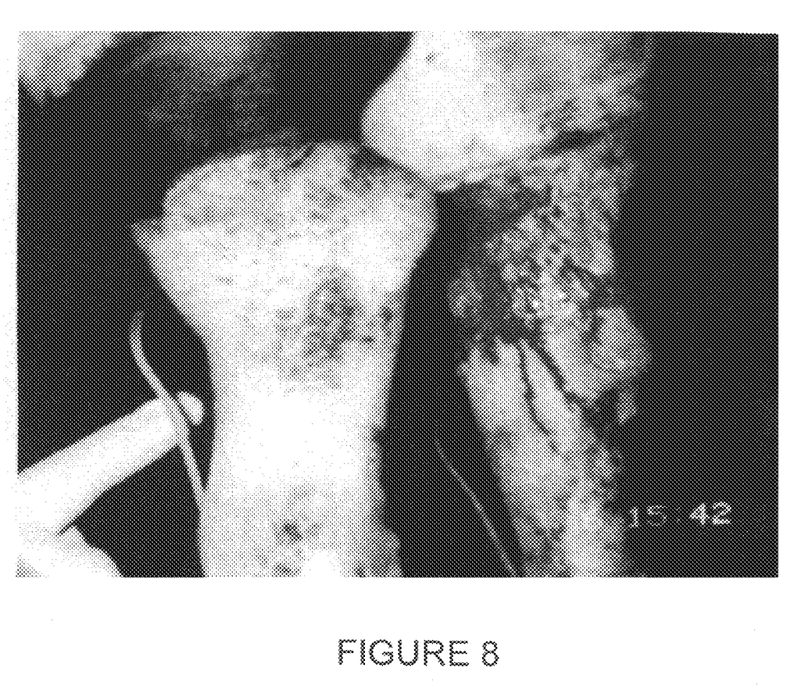
FIG. 8 demonstrates the post enzymatic escharotomy-debridement of the right limb, compared to the control left limb.
Figure 9:
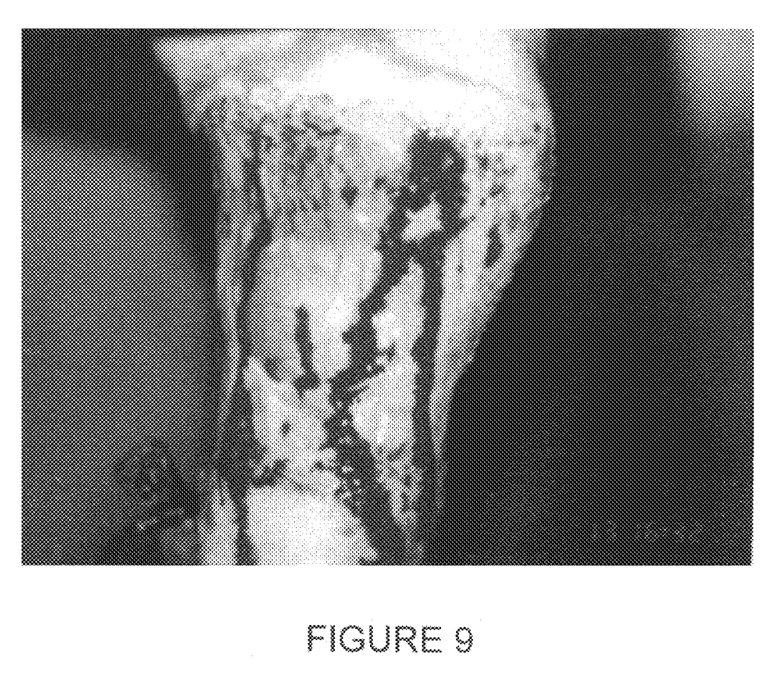
FIG. 9 is a close up of the escharotomized-debrided circular burn illustrating the efficacy of the debridement with exposure of the muscle through the digested fascia
Figure 10:
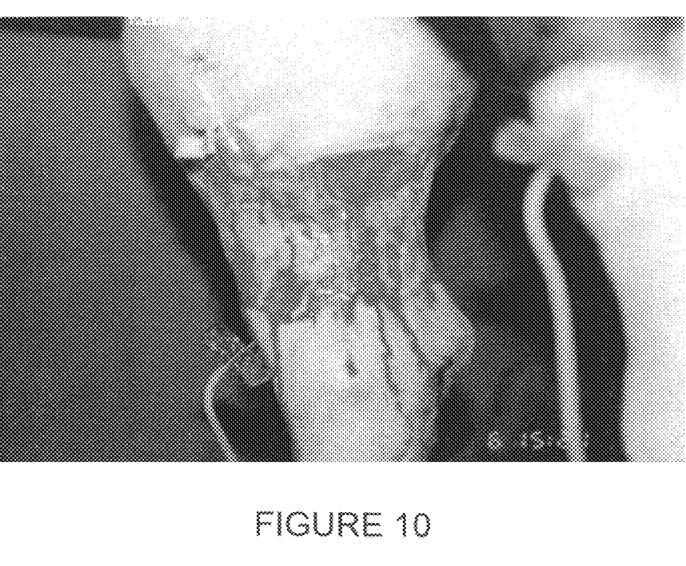
FIG. 10 is a close up of the escharotomized-debrided circular burn illustrating the efficacy of the debridement with exposure of the muscle through the digested fascia.

The burned limbs of an anesthetized experimental animal are shown in FIG. 7. Post enzymatic escharotomy-debridement of the right limb, compared to the control left one is shown in FIG. 8. Two close up views of the escharotomized-debrided circular burn illustrating the efficacy of the debridement with exposure of the muscle through the digested fascia, are presented in FIG. 9 and FIG. 10.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention. Thus the expressions "means to . . . " and "means for . . . ", or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

1. Press B. Thermal, electrical and chemical injuries. In Aston S J, Beasley R W, Thorne C H M (ed): Grabb and Smith's plastic surgery, Lippincott-Raven, 1997, Ch. 16.
2. Blocker T G, Moyer C A, cited by Brunner J. Delayed coverage of the burn wound and joint motion. In Womack N A (ed): On Burns. Springfield Ill., Charles C. Thomas, 1953, p. 172.
3. Hensyl W R (ed). Stedman's medical dictionary.$25^{th}$ edition. Baltimore: Williams & Wilkins, 1990: 1525.
4. Saffle J R, Zeluff G R, Warden G D. Intramuscular pressure in the burned arm: measurement and response to escharotomy. Am J Surg 1980;140:825-831.
5. Dominic W J, Field T O Jr, Hansbrough J F. Comparison of wick and fiber optic catheters in measurement of interstitial pressures in burned extremities. Burns 1988;14:125-129.
6. McQueen MM, Court-Brown C M. Compartment monitoring in tibial fractures—the pressure threshold for decompression. J Bone Joint Surg 1996;78b:99-104.
7. Krisek et al., Orthop. Rev. p.53 July 1975.
8. Levick et al., Burns 4, 281-284, 1977).
9. Klasen H J. A review on the nonoperative removal of necrotic tissue from burn wounds. Burns 2000;26:207-222 reported 10.
10. Salisbury R E, McKeel D W, Mason A D. Ischemic necrosis of intrinsic muscles of the hand after thermal injuries. J Bone Joint Surg 1974;56A:1701-1707.
11. Monafo W W, Brentano L, Gravens D L. Gas Gangrene and mixed clostridian infections of muscle complicating deep thermal burns. Arch Surg 1966;92:212-221.
12. Bardakjian V B, Kenney J G, Edgerton M T, Morgan R F. Pulse Oximetry for vascular monitoring in burned upper extremities. J Burn Care Rehab 1988;9:63-65.

13. Meyer W, Schwartz R, Neurand K. The skin of domestic mammals as a model for the human skin with special reference to the domestic pig. Curr Probl Dermatol 1978; 7:39-52.
14. Rigal C, Pieraggi M T, Serre G, Bouissou H. Optimization of a model of full-thickness epidermal burns in the pig and immunohistochemical study of epidermo-dermal junction regeneration during burn healing. Dermatology 1992;184: 103-110.
15. Hoekstra M J, Hupkens P, Dutrieux R P et al. A comparative burn wound model in the New Yorkshire pig for the histopathlogical evaluation of local therapeutic regimens. British J Plast Surg 1993;46:585-589.
16. Barns T A, Dutrieux R P, Hoekstra M J, Kreis R W, du Pont J S. Histopathological evaluation of scalds and contact burns in the pig model. Burns 1994;20(1):S48-S51.
17. Swindle M M. Anesthetic and perioperative techniques in swine: an update. Spring 1994. Charles River Laboratories Publications.

The invention claimed is:

1. A burn treatment apparatus for treating or relieving burn induced compartment syndrome in a burned limb, said apparatus comprising:
   (a) a flexible, water-impermeable, generally cylindrical or tube shaped covering layer, said covering layer having an inner surface facing the limb and an outer surface, said covering layer having a proximal sealable open end through which the burned limb is inserted and a distal closed end; and
   (b) a lyophilized powder contained within said covering layer, said lyophilized powder comprising (i) at least one enzymatic escharotomy agent, and (ii) excipients, said excipients including at least one viscosity enhancing agent selected from the group consisting of synthetic polymers, natural polymers and combinations thereof;
   wherein said at least one viscosity enhancing agent is capable of forming a viscous solution or suspension from the lyophilized powder upon the addition of a hydrating means;
   wherein said covering is capable of retaining said powder comprising said enzymatic escharotomy agent in close proximity to the burned limb; and
   wherein said covering is capable of retaining said viscous solution or suspension formed upon the addition of said hydrating means.

2. The apparatus according to claim 1, wherein said apparatus further comprises an external dressing layer adjacent or attached to the outer surface of said covering layer, wherein said external layer comprises at least one of a heat retaining cover, an elastic net or a pressure bandage.

3. The apparatus according to claim 1, further comprising a hydrating means.

4. The apparatus according to claim 3, wherein the hydrating means further comprises a chemical debriding agent.

5. The apparatus of claim 4, wherein said chemical debriding agent is selected from the group consisting of acetic acid, pyruvic acid, phosphoric acid, salicylic acid, benzoic acid and malic acid.

6. The apparatus according to claim 1, wherein said lyophilized powder is contained within an adsorbent layer adjacent to the inner surface of said covering layer.

7. The apparatus according to claim 1, wherein said enzymatic escharotomy agent is a proteolytic enzyme selected from the group consisting of:
   bromelain, debridase, collagenase, papain, streptokinase, sutilains, fibrinolysin, fibrinolysin-deoxyribonuclease, a proteolytic enzyme derived from krill, trypsin and combinations thereof.

8. The apparatus according to claim 1, wherein said enzymatic escharotomy agent is a proteolytic enzyme derived from pineapple selected from the group consisting of: bromelain and debridase.

9. The apparatus according to claim 1, wherein the one or more excipients are selected such that the viscous solution or suspension is formed as a gel.

10. The apparatus according to claim 1, wherein the one or more excipients are selected such that the viscous solution or suspension is formed as an emulsion.

11. The apparatus according to claim 1, wherein said covering layer is a sleeve-like dressing.

12. The apparatus according to claim 1, wherein said apparatus is enclosed within a sterile sealed package evacuated from moisture.

13. A method for inducing enzymatic escharotomy of a circumferential burn in an affected limb comprising the steps of:
   (a) enclosing the limb within the burn treatment apparatus of claim 1; and
   (b) activating said enzymatic escharotomy agent in situ by contacting said enzymatic escharotomy agent with hydrating means,
   thereby inducing enzymatic escharotomy of said circumferential burn.

14. The method according to claim 13, wherein said hydrating means is physiological saline or sterile water.

15. The method according to claim 14, wherein said hydrating mean is heated to 34-38° C. prior to contacting of said hydrating mean with said enzymatic escharotomy agent.

16. A method for treating Burn Induced Compartment Syndrome in a burned limb comprising the steps of:
   (a) enclosing the limb within the burn treatment apparatus of claim 1; and
   (b) activating said enzymatic escharotomy agent in situ by contacting said enzymatic escharotomy agent with hydrating means,
   thereby treating the Burn Induced Compartment Syndrome in said burned limb.

17. The method according to claim 16, wherein said hydrating means is physiological saline or sterile water.

18. The method according to claim 17, wherein said hydrating means is heated to 34-38° C. prior to contacting of said hydrating means with said enzymatic escharotomy agent.

* * * * *